United States Patent [19]
Bonjouklian et al.

[11] Patent Number: 5,292,647
[45] Date of Patent: Mar. 8, 1994

[54] STRAIN OF STREPTOMYCES FOR PRODUCING AVERMECTINS AND PROCESSES THEREWITH

[75] Inventors: Rosanne Bonjouklian, Indianapolis; Otis W. Godfrey, Greenwood; Tim A. Smitka, Indianapolis; Raymond C. Yao, Carmel, all of Ind.

[73] Assignee: Eli Lilly and Company, Indianapolis, Ind.

[21] Appl. No.: 984,078

[22] Filed: Nov. 30, 1992

[51] Int. Cl.$^5$ .................. C12P 17/18; C12P 17/02; C12N 1/20; A01N 43/02
[52] U.S. Cl. .................. 435/119; 435/253.5; 435/123; 514/450
[58] Field of Search .............. 435/100, 119, 235.5, 435/123; 514/450, 30

[56] References Cited

U.S. PATENT DOCUMENTS

| | | |
|---|---|---|
| 4,310,519 | 1/1982 | Albers-Schonberg et al. .... 424/181 |
| 4,378,353 | 3/1983 | Goegelman et al. ............. 424/181 |
| 4,429,042 | 1/1984 | Albers-Schonberg et al. .... 435/119 |
| 5,015,662 | 5/1991 | Chen ........................ 514/450 |

FOREIGN PATENT DOCUMENTS

| | | | |
|---|---|---|---|
| 214731 | 7/1986 | European Pat. Off. ... | C07D 493/22 |
| 276103 | 1/1988 | European Pat. Off. ....... | C12P 19/62 |
| 276131 | 7/1988 | European Pat. Off. ..... | C07H 19/02 |
| 284176 | 9/1988 | European Pat. Off. ....... | C12P 19/62 |

OTHER PUBLICATIONS

Miller, T. W. et al., *Antimicrob. Agents Chemother*, 15(3): 368–371 (1979).
*ATCC Catalogue of Bacteria and Bacteriophages*, 18th ed. (1992).

Primary Examiner—David M. Naff
Assistant Examiner—Jeffrey J. Seuigmy
Attorney, Agent, or Firm—Steven A. Fontana; Leroy Whitaker

[57] ABSTRACT

A new microorganism, *Streptomyces avermitilis* subspecies *niger* NRRL 21005, and processes using the microorganism for producing known avermectins are provided.

6 Claims, 2 Drawing Sheets

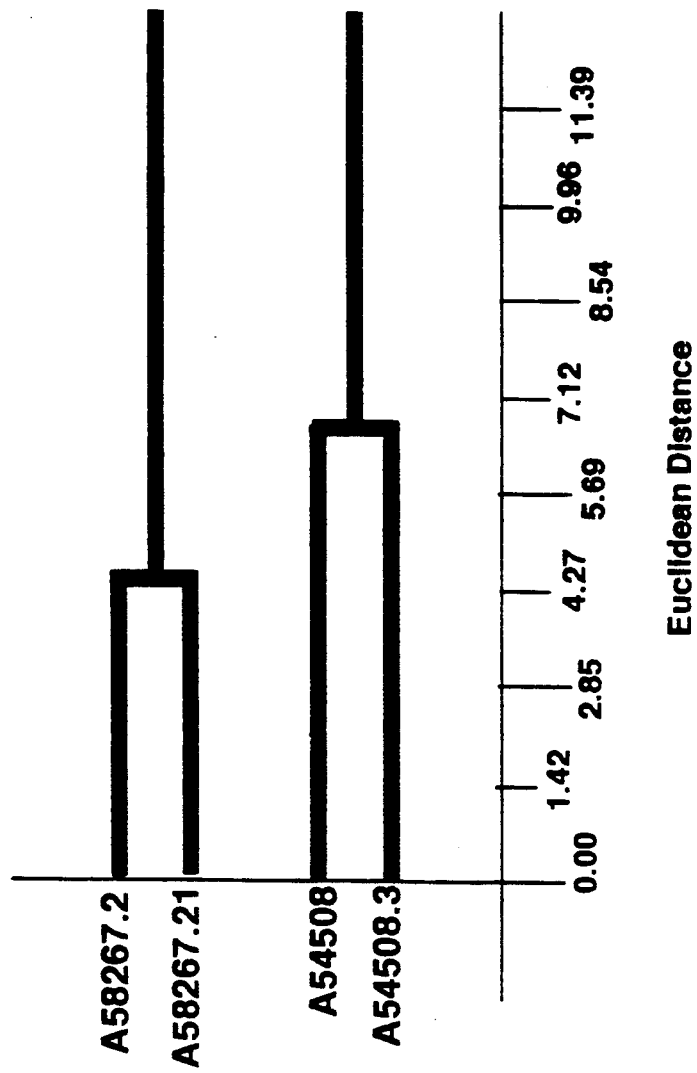

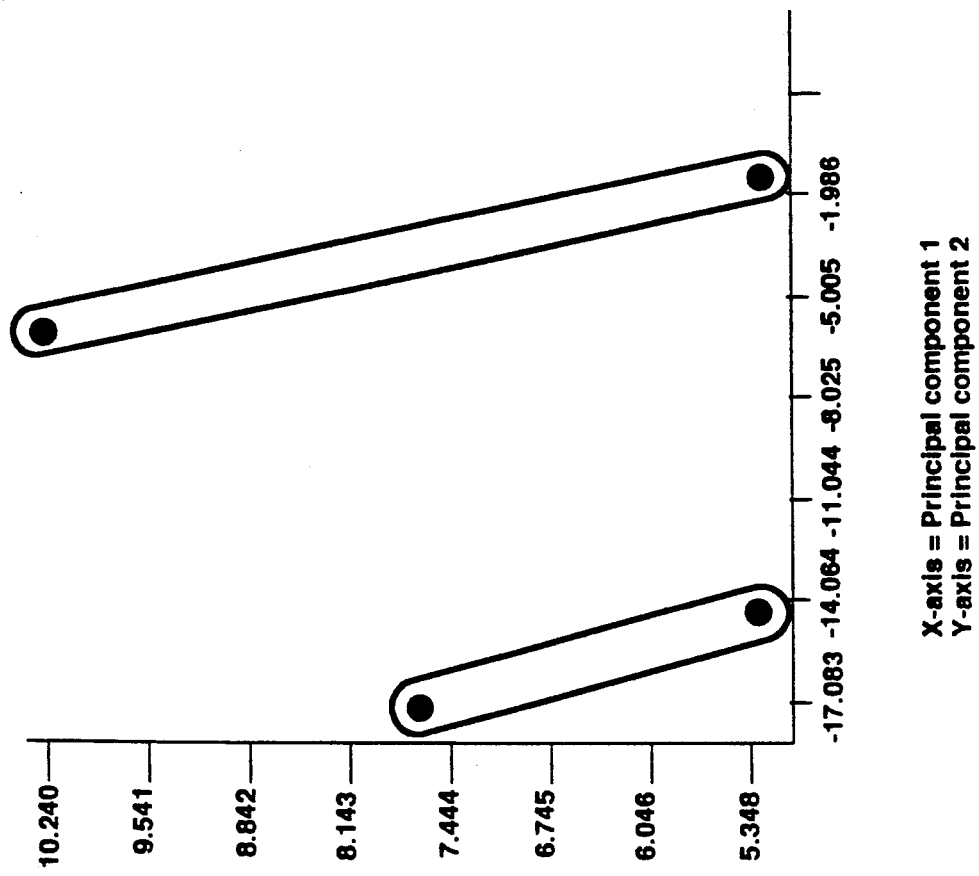

STRAIN OF STREPTOMYCES FOR PRODUCING AVERMECTINS AND PROCESSES THEREWITH

BACKGROUND OF THE INVENTION

Avermectins, a complex of related agents having antiparasitic activity, are known to be produced by aerobic fermentation of *Streptomyces avermitilis* strains ATCC 31267, 31271 and 31272, e.g., U.S. Pat. Nos. 4,310,519 and 4,429,042. The last two strains cited represent a frozen vial and a lyophilized tube, respectively, of a culture obtained by ultraviolet irradiation of *S. avermitilis* ATCC No. 31267.

The strains of *S. avermitilis* cited in the above-mentioned U.S. patents produce a class of substances generically described as C-076 (avermectins, formula I below). The class comprises eight distinct but closely related compounds described as avermectin A1a, A1b, A2a, A2b, B1a, B1b, B2a and B2b. The "a" series of compounds refers to the natural avermectins wherein the 25-position substituent is (S)-sec-butyl, and the "b" series to those natural avermectins wherein the 25-position substituent is isopropyl. The designations "A" and "B" refer to avermectins wherein the 5-position substituent is methoxy or hydroxy, respectively. Lastly, the numeral "1" refers to avermectins wherein a double bond is present at the 22-23 position; and the numeral "2" refers to avermectins having a hydrogen at the 22-position and hydroxy at the 23-position.

Thus, the avermectins are compounds of formula I:

producing one or more of the avermectin compounds only include the parent strain and its progeny.

One other *S. avermitilis* strain, ATCC 53814, has been described in the literature (U.S. Pat. No. 5,015,662). This strain has been distinguished by its ability to bioconvert a series of milbemycin-type compounds, and its inability to produce substantial quantities of avermectins.

The present invention provides a novel avermectin-producing strain, *Streptomyces avermitilis* subspecies *niger* NRRL 21005. The present invention further provides novel processes for the production of avermectins using *Streptomyces avermitilis* subspecies nger NRRL 21005.

SUMMARY OF THE INVENTION

The present invention relates to a biologically pure culture of the microorganism *Streptomyces avermitilis* subspecies *niger* NRRL 21005, or an avermectin-producing mutant or variant thereof.

The present invention further relates to a process for producing one or more avermectins which comprises cultivating *Streptomyces avermitilis* subspecies *niger* NRRL 21005, or an avermectin-producing mutant or variant thereof, in an aqueous culture medium containing assimilable sources of carbon, nitrogen and inorganic salts under submerged aerobic conditions until one or more avermectins are produced, and recovering said avermectin or avermectins.

DESCRIPTION OF THE DRAWINGS

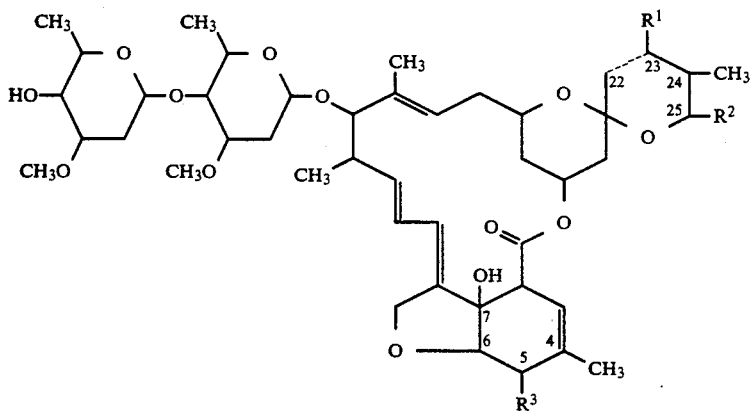

formula I wherein:
the broken line indicates a single or a double bond;
$R^1$ is hydroxy and is only present when said broken line is a single bond;
$R^2$ is isopropyl or sec-butyl; and
$R^3$ is methoxy or hydroxy.

Other strains of *S. avermitilis* are known to produce one or more known or "natural" avermectins, wherein the 25-position substituent is either isopropyl or (S)-sec-butyl(1-methylpropyl), or "non-natural" avermectins wherein the 25-position substituent is other than isopropyl or (S)-sec-butyl. For example, *S. avermitilis* ATCC 31780 is disclosed in U.S. Pat. No. 4,378,353; ATCC 53567 and ATCC 53568 are described in European Patent Application (EP) 276 131; ATCC 53692 is discussed in EP 276 103; and a description of NCIB 12121 is found in EP 214 731 However, each of these *Streptomyces avermitilis* strains are direct or indirect progeny of the *S. avermitilis* ATCC 31267 strain. Thus, the above-referenced *S. avermitilis* strains which are capable of FIG. 1 shows a dendrogram of *Streptomyces avermitilis* subspecies *niger* NRRL 21005 (A58267.2) and other *Streptomyces avermitilis* species.

FIG. 2 shows a principal component plot from fatty acid analysis showing relationships between A58267.2 and *Streptomyces avermitilis* species.

DETAILED DESCRIPTION OF THE INVENTION

One aspect of the present invention pertains to a biologically pure culture of the microorganism *Streptomyces avermitilis* subspecies *niger* NRRL 21005 (the NRRL 21005 strain), or an avermectin-producing mutant or variant thereof.

The new microorganism of this invention, which produces avermectins, is also called culture A58267.2 for convenience. Culture A58267.2 is an improved strain of culture A58267.21 which is a natural variant of culture A58267. Culture A58267 was isolated from a soil sample collected in Italy.

A culture of A58267.2 has been deposited in compliance with the Budapest Treaty, and made part of the stock culture of the Northern Regional Research Center, Agricultural Research Service, North Central Region, United States Department of Agriculture, 1815 North University Street, Peoria, Ill. 61604, from which it has been assigned the accession number NRRL 21005 The permanency of the deposit of this culture at the Northern Regional Research Center at Peoria, Ill., and ready accessibility thereto by the public are afforded throughout the effective life of any patent granted on the application. Access to the cultures is available during pendency of the application under 37 C.F.R. §1.14 and 35 U.S.C. §112. All restrictions on the availability to the public of the cultures will be irrevocably removed upon granting of the patent Taxonomic studies of A58267.2 (NRRL 21005) were conducted by Frederick P. Mertz of the Lilly Research Laboratories. Based on these studies, the new microorganism is classified as a new subspecies (strain) of the genus and species *Streptomyces avermitilis* for which the name *Streptomyces avermitilis* subspecies *niger* is proposed. This classification is based on direct laboratory classification and examination of published descriptions of similar species.

METHODS USED

Taxonomic studies were made using methods recommended by the International Streptomyces Project (ISP) for the characterization of the Streptomyces species [Shirling, E. B. and Gottlieb, D., "Methods for characterization of Streptomyces species," *Int. J. Syst. Bacteriol.*, 16: 313-340 (1966)] and those recommended for the characterization of Nocardia species [Gordon, R. E., Barnett, D. A., Handerhan J. E., and Pang, C. H., "*Nocardia coeliaca, Nocardia autotrophica,* and the Nocardin strain," *Int. J. Syst. Bacteriol.*, 24(1): 54–63 (1974)].

ISCC-NBS Centroid Color Charts, standard sample No 2106 (National Bureau of Standards, 1958, U.S. Department of Commerce, Washington, D.C.), were used to assign color names.

Morphology was studied using an optical light microscope and a scanning electron microscope (SEM).

The isomer of diaminopimelic acid (DAP) and the carbohydrates in hydrolysates of whole cells were established by the chromatographic methods of Becker, et al., "Rapid Differentiation between Nocardia and Streptomyces by Paper Chromatography of Whole-cell Hydrolysates", *Appl. Microbiol.*, 12: 421–423 (1964) and of Lechevalier, et al., *A University Laboratory Approach,* Dietz and Thayer (eds.), Society for Industrial Microbiology, Special Publication No. 6, Arlington, Va., pp. 227–233.

Resistance to antibiotics was measured by padding antibiotic sensitivity discs onto the surface of seeded ISP No. 2 agar plates Resistance was scored as (+) when no zone of inhibition was observed and as (−) when a zone of inhibition was observed Menaquinone composition was determined by following the procedures of Kroppenstedt, R. M., "Chemical Methods in Bacterial Systematics, M. Goodfellow and D. E. Minnikin (eds.), pp. 173–196 (1985); and Collins, M. D., id., pp. 267–285.

Fatty acid analysis was accomplished using the HP 5898A Microbial Identification System of Miller, L., et al., "Bacterial Identification by Gas Chromatography of Whole-Cell Fatty Acids", Hewlett-Packard Application Note 228–41, pp. 8 (1985).

Fatty acid methyl esters were made from lyophilized whole cells grown under identical conditions.

NaCl tolerance was measured by adding NaCl to ISP No. 2 agar to equal the concentration desired.

The dendrogram shown in FIG. 1 is based on Euclidean distance and was computer generated.

The principal component analysis shown in FIG. 2 is two-dimensional and was also computer generated.

CULTURAL CHARACTERISTICS

Culture A58267.2 does not grow well on most media and produces no aerial hyphae on either complex or defined media. The color of the reverse side is yellow-brown except when grown on Bennetts agar where a distinctive black pigment is produced. A faint light brown soluble pigment is produced in ISP medium 2, and a reddish-brown soluble pigment is produced in Bennetts agar. Table 1 presents these cultural characteristics.

TABLE 1

| MEDIUM | Growth | Reverse Color | Aerial Growth | Aerial Color | Soluble Pigment |
|---|---|---|---|---|---|
| ISP medium 2 | good | 80.gy. yBr. | none | none | light-Br. |
| ISP medium 3 | poor | 78. d. yBr. | none | none | none |
| ISP medium 4 | fair | 93. y. Gray | none | none | none |
| ISP medium 5 | none | none | none | none | none |
| ATCC medium 172 | none | 78. d. yBr. | none | none | none |
| Bennetts agar | abundant | 65. br. Blk | none | none | reddish-Br. |
| Calcium-malate | poor | 90. gy. Y. | none | none | none |
| Cotton seed agar | fair | 91. d. gy.Y | none | none | none |
| Czapeks | none | none | none | none | none |
| Glucose-asparagine | none | none | none | none | none |
| Glycerol-glycine | none | none | none | none | none |
| Humic acid agar | none | none | none | none | none |
| NPBM[2] | abundant | 78. d. yBr. | none | none | none |
| Nutrient agar | poor | 91. d. gy.Y | none | none | none |
| Starch casein agar | fair | 91. d. gy.Y | none | none | none |
| Tomato-paste-oatmeal | none | none | none | none | none |
| Tap water agar | none | none | none | none | none |
| Yeast-dextrose agar | abundant | 90. gy. Y. | none | none | reddish-Br. |

[1] Incubated at 30° C. for 18 days
[2] NPBM = Nutrisoy flour 5 gm., Peanut meal 5 gm., Black strap molasses 5 gm., Distillers grains 5 gm., Oatmeal 5 gm., Glycerol 1 gm., Potato dextrin 5 gm., Czapeks mineral mix 2 mLs., Deionized water 1 liter.

MORPHOLOGICAL CHARACTERISTICS

Aerial hyphae are not produced by culture A58267 2. Consequently, morphological and spore surface studies could not be done. Sporangia, motile cells, or sclerotia were not observed. Culture A58267.2 does not fragment during growth on solid or liquid media.

PHYSIOLOGICAL CHARACTERISTICS

Culture A58267.2 utilized the following carbohydrates with ISP medium 9 as the basal medium D and L-arabinose, cellobiose, D-fructose, D-galactose, D-glucose, glycerol, glycogen, iso-inositol, inulin, D-maltose, D-mannitol, D-mannose, melebiose, D-raffinose, L-rhamnose, D-ribose, trehalose, xylitol, and D-xylose. Culture A58267.2 was unable to utilize the following carbohydrates with ISP medium 9 as the basal medium: adonitol, cellulose, dextrin, dulcitol, ethanol, iso-erythritol, D-lactose, melizitose, a-methyl-D-glucoside, salicin, sorbitol, L-sorbose, and sucrose.

A58267.2 decomposed adenine, calcium malate, casein, starch, and urea.

A58267.2 produced catalase, $H_2S$ and liquefied gelatin, and was able to survive exposure to 50° C. for 8 hours. A58267.2 tolerated NaCl at levels up to and including 6%.

A58267.2 was unable to hydrolyze allantoin, elastin, esculin, guanine, hippurate, hypoxanthine, testosterone, L-tyrosine, or xanthine. It did not produce melanoid pigments, reduce nitrates, or produce phosphatase, nor was it resistant to lysozyme at a concentration of 50 mg/mL.

Culture A58267.2 was resistant to 2 μg [micrograms] of lincomycin, 30 μg of nalidixic acid, 10 units of penicillin G, 300 units of polymixin B, and 5 μg of trimethoprim. A58267.2 was sensitive to 10 units of bacitracin, 30 μg of cephalothin, 30 g of chloromycetin, 15 μg of erythomycin, 10 μg of gentamycin, 30 μg of neomycin, 30 μg of novobiocin, 15 μg of oleandomycin, 5 μg of rifampin, 10 μg of streptomycin, 30 μg of tetracycline, 10 μg of tobramycin, and 30 μg of vancomycin.

Culture A58267.2 grew in a temperature range from 15° to 37° C. An optimal growth temperature appeared to be about 30° C.

CELL WALL ANALYSIS

Cell wall analysis of parent strain A58267.21 demonstrated that hydrolyzed whole cells contain LL-diaminopimelic acid (DAP). Sugars present in the whole cell extracts were glucose and ribose. The fatty acid type is 2C, while the major menaquinone is MK-9 ($H_6$). The measurements represent a typical cell wall type for the genus Streptomyces and are expected to be similar for the A58267.2 strain.

IDENTITY OF STRAIN A58267.2

Culture A58267.2 is believed to have a type I cell wall, type NC whole sugar pattern, and a menaquinone composition primarily of MK-9 ($H_6$). These chemotaxonomic properties and the cultural and morphologic characteristics of A58267.2 support the assignment of the isolate to the genus Streptomyces [see, Lechevalier, et al., "Chemical Composition as a Criterion in the Classification of Aerobic Actinomycetes, *Int. J. Syst. Bacteriol.*, 20; 435–443 (1970)].

Although 11 strains of *Streptomyces avermitilis* are disclosed in the ATCC "Catalogue of Bacteria and Bacteriophages", 18th edition (1992), *S. avermitilis* ATCC 31267 is identified throughout the literature as the direct or indirect parent of 10 of the 11 strains. When ATCC 31267 (A54508) is not the direct parent strain, a first generation progeny,. ATCC 31272 (A54508 3), is frequently the direct parent strain. The literature descriptions of progeny of either ATCC 31267 or 31272 indicate that the progeny generally share the characteristics of the parent strain, but contain some minor differentiating characteristic(s) (see, e.g., the taxonomic description of ATCC 53567 and 53568 in E.P. 276 131). Thus, the direct or indirect parent strain of all but one known *S. avermitilis* strain, ATCC 31267/A54508, and one of its first generation progeny (ATCC 31272/A54508.3) were selected as the strains to which the ATCC 21005 (A58267.2) strain was compared.

In one highly determinative comparison, fatty acid analysis was conducted on A58267.2, A54508 and A54508.3. Table 2 presents a comparison of the percentage of specific fatty acids found in each strain.

TABLE 2

| Fatty acid composition of A58267.2 and two *Streptomyces avermitilis* strains[1]. | | | |
|---|---|---|---|
| FATTY ACID | A58267.2 | A54508 | A54508.3 |
| 14:0 Iso (Iso myristic acid) | 3.36 | 7.95 | 4.67 |
| 15:0 Iso | 22.30 | 11.11 | 11.24 |
| 15:0 Anteiso | 19.29 | 21.41 | 22.99 |
| 15:0 (Pentadecanoic acid) | 2.45 | 2.08 | 2.17 |
| 16:1 Iso H | 4.23 | 4.68 | 1.96 |
| 16:0 Iso (Iso Palmitic acid) | 14.02 | 19.85 | 16.43 |
| 16:1 Cis 9(Palmitoleic acid) | 3.93 | 3.31 | 2.82 |
| 16:0 (Palmitic acid) | 4.53 | 3.26 | 5.14 |
| 17:1 Iso F | 7.57 | 6.07 | 6.27 |
| 17:1 Anteiso C | 3.42 | 3.56 | 3.07 |
| 17:0 Iso (Iso Margaric acid) | 5.51 | 5.12 | 7.83 |
| 17:0 Anteiso | 5.88 | 8.23 | 11.93 |

[1]Cells were grown for 4 days in TSB at 28° C.

A computer generated dendrogram constructed from fatty acid profiles is presented in FIG. 1. This dendrogram demonstrates the relationship of A58267.2 to the other *Streptomyces avermitilis* strains, as shown by Euclidean distance. Cultures showing relatedness below the level of 10.00 are interpreted as being synonymous, that is, of the same species. A58267.2 is related to *S. avermitilis* at a level above 10.00.

Principal component analysis is a branch of multivariate statistics which deals with internal relationships of a set of variables. In this analysis, the greatest amount of variance within the original data or test results is expressed as principal components [Alderson, G., "The Application and Relevance of Nonhierarchic Methods in Bacterial Taxonomy", in *Computer-assisted Bacterial Systematics*, Goodfellow, M., et al. (eds.), Academic Press, New York (1985)]. Thus, a plot showing scatter or variability can be constructed. Relationships can then be evaluated by examining this variance, and a microbial population can be characterized. A two-dimensional principal component plot based on fatty acids was constructed showing the relationship of culture A58267 2, and its parent strain A58267.21, to the other *S. avermitilis* species. These data are presented in FIG. 2.

In both the dendrogram and the principal component plot, two distinct clusters are formed. A58267.2 and A58267.21 form one cluster, whereas A54580 and A54580.3 form another cluster. These two clusters are sufficiently similar to indicate that the strains in the two clusters are related, but also sufficiently different to demonstrate that neither the clusters nor the individual strains are identical.

A review of the differences between A58267.2 and A54840.3 is presented in Table 3.

TABLE 3

Differences between S. avermitilis strains A58267.2 and A54580.3

| CHARACTERISTIC | A58267.2 | A54580.3 |
| --- | --- | --- |
| Aerial spore production | − | − |
| Growth on calcium malate agar | − | + |
| Reverse pigment production on Bennetts agar | black | brown |
| Soluble pigment production on Yeast dextrose agar | + | − |
| Antibiotic resistance: | | |
| lincomycin | + | − |
| polymixin B | + | − |
| Growth in 7% NaCl | − | + |
| Decomposition of: | | |
| esculin | − | + |
| hippurate | − | + |
| hypoxanthin | − | + |
| xanthine | − | + |
| Lysozyme resistance 50 µg/mL. | − | + |
| Melanoid pigment production | − | + |
| Nitrate reduction | − | + |
| Acid production from raffinose | + | − |
| Fatty acid composition, %: | | |
| 15.0 Iso | 22.30 | 11.24 |
| 15:0 Anteiso | 19.29 | 22.99 |
| 16:1 Iso H | 4.23 | 1.96 |
| 16:0 Iso | 14.02 | 16.43 |
| 17.0 Iso | 5.51 | 7.83 |
| 17:0 Anteiso | 5.88 | 11.93 |

As previously stated, there are insufficient differences between S. avermitilis strains A58267.2 and A5450-8/A54508 3 to establish A58267.2 as a separate species. There are, however, sufficient differences between these strains to establish A58267.2 as a distinct and separate subspecies (strain) of the known Streptomyces avermitilis strains Thus, A58267.2 is established as a subspecies of S. avermitilis and is classified as Streptomyces avermitilis subspecies niger NRRL 21005 The subspecies name niger refers to the distinctive color exhibited on Bennetts agar.

Another aspect of the present invention provides a process for producing one or more avermectins which comprises cultivating Streptomyces avermitilis subspecies ner NRRL 21005, or an avermectin-producing mutant or variant thereof, in an aqueous culture medium containing assimilable sources of carbon, nitrogen, and inorganic salts under submerged aerobic conditions until one or more avermectins are produced, and recovering said avermectins. The produced avermectins can be recovered using various isolation and purification procedures known in the art.

As is the case with other microorganisms, the characteristics of the avermectin-producing culture of this invention, Streptomyces avermitilis subspecies niger NRRL 21005, is subject to variation. Mutants of the strain may be obtained by methods known in the art, for example, by treatment with various physical and chemical mutagens such as ultravillet light, X-rays, gamma rays and chemicals such as n-methyl-N'-nitro-N-nitrosoguanidine. Natural variants of the strain may also be obtained by methods known in the art, for example, screening cultures of the parent strain. Natural variants and induced mutants of S. avermitilis subspecies niger NRRL 21005, which retain the characteristics of avermectin production are considered part of this invention.

The culture medium used to grow the S. avermitilis culture of the present invention can be any one of a number of media. Thus, for example, preferred carbohydrate sources in large-scale fermentations are glucose, mannose and, especially, potato dextrin. However, other carbohydrate courses such as ribose, xylose, fructose, galactose, mannitol and the like can be used.

A preferred nitrogen source is soybean flour although enzyme or acid hydrolyzed casein, yeast, liver meal, meat peptones, fish meal and the like are also useful.

Nutrient inorganic salts which can be incorporated into the culture medium include the customary soluble salts capable of yielding zinc, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other components of the medium in amounts sufficient to meet the growth requirements of the organism. If foaming is a problem, small amounts (e.g., 0.2 gm/L) of an anti-foam agent such as polypropylene glycol, having a molecular weight of about 2000, may be added to large-scale fermentation media if needed.

Examples of preferred concentrations of culture media components are shown in Example 1 below.

For production of substantial quantities of avermectins, submerged aerobic fermentation in tanks is preferred. Small quantities of the A58267.2 culture may be obtained by shake-flask culture. Because of the time lag in avermectin production commonly associated with inoculation of large tanks with the spore form organism, it is preferable to use a vegetative inoculum. The vegetative inoculum is prepared by inoculating a small volume of culture medium with the spore form or mycelial fragments of the organism to obtain fresh, actively growing cultures of the organism. The vegetative inocculum is then transferred to a larger vessel, and the production stage of avermectins is initiated. The vegetative inoculum medium can be the same as that used for larger fermentations, but other media are also suitable.

In the process of this invention, avermectins are produced by the A58267.2 organism when grown at temperatures between about 15° C. and about 37° C. An optimum temperature for avermectin production appears to be from about 29° C. to about 31° C.

As is customary in submerged aerobic culture processes, sterile air is blown into the vessel from the bottom while the media is stirred with conventional turbine impellors. The maximum oxygen uptake of the fermentation under the conditions used thus far has not exceeded about 0.16 mM/L/minute. In a fully baffled 115-liter fermentor containing approximately 107 liters of broth, the aeration rate and agitation rate should be sufficient to maintain a level of dissolved oxygen of at least 45% of air saturation with an internal vessel pressure of 5.0 atmospheres.

Production of avermectins can be followed during the fermentation by testing samples of the broth versus known standards via various methods such as HPLC.

Following their production under submerged aerobic fermentation conditions, avermectins can be recovered from the fermentation medium by methods known in the fermentation art. Generally, the avermectins produced during fermentation of the A58267.2 culture or avermectin-producing mutant or variant thereof, occur both in the filtered broth and, particularly, in the mycelial mass. Thus, if avermectins are to be directly fed to animals, the whole fermentation broth may be dried and blended with feed for such animals.

More preferably, the avermectins are separated from the whole fermentation broth, and the recovery of the individual avermectin compounds is carried out by solvent extraction and application of chromatographic fractionations with various chromatographic techniques and solvent systems. Techniques for separation and recovery of avermectins are described in U.S. Pat. No. 4,429,042; and Miller, T. W., et al., *Antimicrob. Agents Chemother.*, 15(3): 368-371 (1979). Preferred techniques for such separation and recovery are presented below in the Examples.

Once produced and isolated, avermectins are particularly useful for treating animals having parasitic infections, and are especially useful as anthelmintics, insecticides and acaricides. This antiparasitic use is well known in the animal health art and is well documented (, e.g., U.S. Pat. Nos. 4,429,042 and 4,310,519).

To illustrate more fully the operations of this invention, the following examples are provided. These examples, however, are not intended to be limiting to the scope of the invention in any respect and should not be so construed.

In the following examples, $^{13}C$ nuclear magnetic resonance spectral data for avermectin compounds A1a, A1b, A2a, A2b, B1a, B1b, B2a and B2b, in deuterated chloroform solution, were obtained from a General Electric Model QE 300 spectrometer (Fremont, Calif.). Solution volume of each sample was about 0.7 mL. Chemical shifts for each avermectin compound, relative to deuterated chloroform, are given in ppm (77 ppm). FABMS data were generated using a ZABII-SE spectrometer (VG Analytical, Manchester, England).

EXAMPLE 1

Fermentation of A58267.2

A. Shake Flask

The culture *Streptomyces avermitilis* subspecies *niger* NRRL 21005, maintained in liquid nitrogen, was used to inoculate (0.5 mL) a first-stage vegetative medium having the following composition:

| Vegetative Medium | |
|---|---|
| Ingredient | Amount (g/L) |
| Tripticase Soy Broth | 30.0 |
| Yeast Extract | 3.0 |
| $MgSO_4.7H_2O$ | 2.0 |
| Glucose | 5.0 |
| Maltose | 4.0 |
| Deionized water q.s. to 50 mL | |

Unadjusted pH = 7.0; pH was not adjusted following sterilization; post-sterilization pH = 6.9.

The inoculated vegetative medium was incubated in a 250 mL wide-mouth Erlenmeyer flask at 30° C. for about 46 hours on a shaker orbiting in a two-inch (5.08 cm) circle at 250 rpm. The flask was protected by two bioshield filters, and the shaker board angle was 0°.

B. Tank Fermentation of A58267.2

To provide a larger volume of inoculum, 10 mL of incubated first-stage medium, prepared as described above in Section A, was used to inoculate 400 mL of a second-stage vegetative medium having the same composition as that of the first-stage medium. This second stage medium was incubated in a 2 L wide-mouth Erlenmeyer flask at 30° C. for about 48 hours on a shaker orbiting in a two-inch (5.08 cm) circle at 250 rpm. This flask also was protected by two bioshield filters, and the shaker board angle was 0°.

This second-stage vegetative medium (400 mL) was used to inoculate 107 L of sterile production medium having the following composition:

| Production Medium | |
|---|---|
| Ingredient | Amount ( /L) |
| Soybean flour | 5.0 g |
| Potato dextrin | 80.0 g |
| Baby oatmeal | 5.0 g |
| Blackstrap molasses | 5.0 g |
| $CaCO_3$ | 2.0 g |
| Glycerol | 1.0 mL |
| Czapek's Mineral Stock | 2.0 mL |
| Deionized water q.s. to 107 L. | |

Unadjusted pH = 6.5; adjusted to pH 7.3 with about 30 mL of 5N NaOH; post-sterilization pH = 7.0.

Antifoam added: SAG 471 at 0.2 gm/L (Union Carbide, Sistersville, West Virginia).

The inoculated production medium was allowed to ferment in a 115 L stirred fermentation tank for between 10 and 11 days at a temperature of 30° C. A dissolved oxygen level of about 45% of air saturation was maintained, as was a low rpm (about 137 to about 255) in the stirred vessel.

EXAMPLE 2

General Isolation of Avermectins

Whole fermentation broth from a 115 L, prepared in a manner similar to that described in Example 1, was adjusted to pH 6.5 with 5N HCL. An equal volume of MeOH was added to the solution and the solution was filtered through a Membralox ceramic filter (U.S. Filter/SCT, Bazet, France). The filtrate was then passed over a column containing 10 L of HP-20SS (Diaion) (Mitsubishi Chemical Industries Ltd., Tokyo, Japan). The column was next eluted with a linear gradient of 50-100% MeOH in water. Collected fractions were analyzed by HPLC over a 4.6 mm (i.d.)×30 cm column containing Dynamax $C_{18}$ (Rainin Company, Woburn, MA). The column was eluted using an isocratic gradient of MeOH:$CH_3CN$:(0.2% HOAc, pH adjusted to 5.0 with NaOH), 44:44:12, with a flow rate of 1.5 mL/min. The fractions were combined into two pools based on the HPLC analysis. The pools were concentrated under reduced pressure to about 500 mL aqueous. The pools were extracted with $CHCl_3$, and the extracts were evaporated to yield 18.25 g oil (Pool A) and 6.48 g oil (Pool B).

EXAMPLE 3

Treatment of Pool A

Pool A (18.25 g) from Example 2 was dissolved in 45 mL MeOH and chromatographed over a 5 cm (i.d.)×1.1 m column containing Sephadex LH-20 (Pharmacia, Piscataway, N.J.). The column was eluted with MeOH and the fractions analyzed by HPLC. Those fractions containing avermectins were combined into two pools and evaporated to yield Pool C (10.96 g) and Pool D (1.45 g).

EXAMPLE 4

Treatment of Pool C

Material from Pool C (2 g from Example 3) was dissolved in 4.5 mL of MeOH and chromatographed over a 41.4 mm (i.d.)×25 cm column containing Dynamax-60A $C_{18}$ (Rainin, Woburn, Mass.). The column was eluted using a linear gradient of $CH_3CN:MeOH:H_2O$), 40:40:20 to 46:46:8 over 100 minutes with a flow rate of 15 mL/min. Four pools were made on the basis of HPLC analysis Pool E (489 mg), Pool F (624 mg), Pool G (656 mg), and Pool H (177 mg).

EXAMPLE 5

Isolation of Avermectin A1a

Pool B from Example 2 was dissolved in 30 mL MeOH and chromatographed as described in Example 3. The column was eluted with MeOH and the fractions analyzed by HPLC. Those fractions containing avermectins were combined and evaporated to a residue (658 mg). A portion (200 mg) of the residue was chromatographed over a 2.5 cm (i.d.)×30 cm column containing Chromegabond MC18 (ES Industries, Berlin, N.J.), using a gradient of $CH_3CN:MeOH:H_2O$, 40:40:20 to 42:42:16 over 90 minutes at a flow rate of 5 mL/min. This method afforded 63 mg of avermectin A1a; MS:FAB m/z=909 $[Aver_{A1a}+Na]^+$; $^{13}C$ NMR (75 MHz, $CDCl_3$) δ 11.96, 12.88, 15.03, 16.30, 17.62, 18.32, 19.82, 20.18, 27.44, 30.50, 34.18, 34.43, 35.13, 36.52, 39.66, 40.41, 45.61, 56.32, 56.41, 57.69, 67.18, 68.07, 68.15, 68.32, 74.83, 76.01, 76.89, 77.41, 78.15, 80.43, 80.50, 81.92, 118.25, 118.31, 119.58, 124.79, 135.10, 135.98, 136.08, 137.58, 139.85, 173.81, 94.88, 98.44, 68.33, 127.74.

EXAMPLE 6

Isolation of Avermectins A2a and B1b

The material from Pool F from Example 4 was dissolved in 2.5 mL MeOH and chromatographed on the column as described in Example 4. The column was eluted isocratically using MeOH $H_2$), 85:15, at a flow rate of 15 mL/min, affording pure avermectin A2a (202 mg); MS:FAB m/z=927 $[Aver_{A2a}+Na]^+$; $^{13}C$ NMR (75 MHz, $CDCl_3$) δ 173.4, 139.83, 137.48, 135.79, 135.60, 124.80, 119.65, 118.43, 117.47, 99.56, 98.41, 94.78, 81.67, 80.50, 80.36, 79.24, 78.15, 77.50, 76.80, 75.90, 70.67, 69.79, 68.25, 68.12, 68.06, 67.55, 67.18, 57.60, 56.38, 45.54, 41.06, 40.70, 39.62, 36.27, 35.61, 35.04, 34.41, 34.26, 34.07, 27.18, 20.20, 19.86, 18.31, 17.65, 15.06, 13.72, 12.37, 11.75; and avermectin B1b (79 mg): MS:FAB m/z=881 $[Aver_{B1b}+Na]^+$; $^{13}C$ NMR (75 MHz, $CDCl_3$) δ 173.56, 139.54, 137.95, 137.80, 135.97, 135.07, 127.72, 124.70, 120.31, 118.28, 118.00, 98.43, 95.63, 94.88, 81.83, 80.38, 80.32, 79.32, 79.22, 78.22, 77.26, 75.96, 68.32, 68.28, 68.24, 68.10, 67.67, 67.21, 56.46, 56.36, 45.66, 40.45, 39.72, 36.63, 34.52, 34.22, 30.88, 28.31, 21.03, 20.18, 19.88, 18.37, 17.68, 16.51, 15.08, 14.86.

EXAMPLE 7

Isolation of Avermectins A1b and B1a

The material from Pool G from Example 4 was dissolved in 3 mL $CH_3CN$ and chromatographed over a 2.5 cm (i.d.)×30 cm column containing Chromegabond MC18 (ES Industries, Berlin, N.J.), using a linear gradient of $CH_3CN:H_2O$, 73:27 to 80:20 over 100 minutes at a flow rate of 5 mL/min in three separate runs, affording pure avermectin A1b (145 mg); MS:FAB m/z=895 $[Aver_A1b+Na]^+$; $^{13}C$ NMR (75 MHz, $CDCl_3$) δ 173.39, 139.61, 137.35, 135.60, 134.87, 127.58, 119.45, 118.29, 118.07, 98.22, 94.41, 94.69, 81.68, 80.29, 80.22, 79.10, 77.99, 77.28, 77.00, 76.65, 75.73, 68.08, 68.05, 67.91, 66.98, 57.43, 56.21, 56.18, 45.39, 40.24, 39.45, 36.36, 34.30, 34.05, 30.65, 28.09, 20.82, 20.03, 19.66, 18.15, 17.48, 16.31, 14.87, 14.64, 124.63; and avermectin B1a (245 mg); MS:FAB m/z=895 $[Aver_{B1a}+Na]^+$; $^{13}C$ NMR (75 MHz, $CDCl_3$) δ 173.40, 139.53, 137.84, 137.70, 136.08, 135.08, 127.74, 124.69, 120.23, 118.23, 117.94, 98.42, 95.69, 94.87, 81.69, 80.23, 80.15, 79.13, 78.05, 75.69, 74.61, 68.12, 68.03, 67.93, 67.46, 67.01, 56.26, 56.17, 45.43, 40.28, 39.51, 36.33, 34.93, 34.23, 34.05, 30.32, 27.25, 19.99, 19.66, 18.14, 17.50, 16.15, 14.85, 12.74, 11.81.

EXAMPLE 8

Isolation of Avermectins A2b, B2a and B2b

The material from Pool E from Example 4 was dissolved in 1.9 mL $CH_3CN$ and chromatographed on the column as described in Example 7. The column was eluted using a linear gradient of $CH_3CN:H_2O$, 65:35 to 75:25 over 100 minutes at a flow rate of 5 mL/min in two separate runs, affording pure avermectin A2b (80 mg); MS:FAB m/z=913 $[Aver_{A2b}+Na]^+$; $^{13}C$ NMR (75 MHz, $CDCl_3$) δ 173.60, 139.83, 137.47, 135.92, 135.54, 124.75, 119.52, 118.21, 117.44, 99.53, 98.37, 94.69, 81.53, 80.43, 80.30, 79.21, 78.10, 77.34, 76.81, 75.92, 72.24, 69.75, 68.24, 68.10, 68.05, 67.45, 67.14, 57.65, 56.38, 56.31, 45.52, 40.99, 40.63, 39.60, 36.37, 35.95, 34.47, 34.14, 27.86, 20.68, 20.16, 19.80, 18.29, 17.59, 15.05, 13.85, 13.55; avermectin B2a (125 mg); MS:FAB m/z=913 $[Aver_{B2a}+Na]^+$; $^{13}C$ NMR (75 MHz, $CDCl_3$) δ173.63, 139.68, 138.01, 135.62, ∼ 135, 124.72, 120.34, 117.92, 117.54, 99.63, 98.47, 94.77, 81.55, 80.35, 79.31, 79.08, 78.17, 76.07, 72.35, 69.86, 68.43, 68.32, 68.10, 67.68, 67.51, 67.25, ∼56.3, ∼56.3, 45.67, 41.11, 40.72, 39.75, 36.55, 36.07, 34.57, 34.24, 34.17, 34.17, 27,96, 20.80, 20.21, 19.97, 18.41, 17.68, 15.17, 13.95, 13.67; and avermectin B2b (145 mg); MS:FAB M/Z=899 $[Aver_{B2b}+Na]^+$; $^{13}C$ NMR (75 MHz, $CDCl_3$) δ 173.09, 139.44, 137.65, 137.57, 135.44, 124.50, 120.90, 117.76, 117.34, 99.41, 98.26, 94.63, 81.47, 80.19, 79.20, 79.10, 78.04, 75.72, 70.57, 69.66, 68.10, 68.03, 67.97, 67.45, 67.36, 67.05, 56.28, 56.24, 45.45, 40.57, 39.52, 36.17, 35.46, 34.90, 34.26, 34.09, 33.91, 27.04, 20.00, 19.69, 18.16, 17.51, 14.91, 13.56, 12.33, 11.59.

We claim:

1. A biologically pure culture of the microorganism *Streptomyces avermitilis* subspecies *niger* NRRL 21005, or an avermectin-producing mutant thereof.

2. The culture of claim 1 which is *Streptomyces avermitilis* subspecies *niger* NRRL 21005.

3. A process for producing at least one avermectin compound which comprises cultivating *Streptomyces avermitilis* subspecies *niger* NRRL 21005, or an avermectin-producing mutant thereof, in an aqueous culture medium containing sources of assimilable carbon, nitrogen and inorganic salts under submerged aerobic conditions until at least one avermectin compound is produced, and recovering said avermectin.

4. The process of claim 3 wherein said avermectin compound is selected from the group consisting of A1a, A1b, A2a, A2b, B1a, B1b, B2a and B2b.

5. The process of claim 3 wherein *Streptomyces avermitilis* subspecies *niger* NRRL 21005 is used.

6. The process of claim 3 which includes the additional step of separating individual avermectins recovered from said culture medium.

* * * * *